(12) United States Patent
Telles et al.

(10) Patent No.: US 7,118,543 B2
(45) Date of Patent: Oct. 10, 2006

(54) ORTHOSIS CLOSURE SYSTEM WITH MECHANICAL ADVANTAGE

(75) Inventors: Jeffrey L. Telles, Tracy, CA (US); Craig J. Koloske, Tracy, CA (US); Chad M. Sindel, Walnut Creek, CA (US)

(73) Assignee: Top Shelf Manufacturing, LLC, Stockton, CA (US)

( * ) Notice: Subject to any disclaimer, the term of this patent is extended or adjusted under 35 U.S.C. 154(b) by 0 days.

(21) Appl. No.: 10/936,762

(22) Filed: Sep. 9, 2004

(65) Prior Publication Data

US 2005/0054960 A1 Mar. 10, 2005

Related U.S. Application Data

(60) Provisional application No. 60/501,026, filed on Sep. 9, 2003.

(51) Int. Cl.
*A61F 5/00* (2006.01)

(52) U.S. Cl. ............... 602/19; 602/5; 602/32; 602/12; 128/96.1; 128/100.1; 2/311

(58) Field of Classification Search ........... 602/12, 602/19, 5, 32; 128/96.1, 95.1, 98.1, 99.1, 128/100.1, 101.1, 105.1, 106.1, 107.1; 2/44, 2/45, 92, 311; 24/713.4, 713.5, 714.6, 715, 24/715.1, 715.2, 713.6; 36/50.1
See application file for complete search history.

(56) References Cited

U.S. PATENT DOCUMENTS

| 321,145 | A | * | 6/1885 | Spencer | 24/713.5 |
|---|---|---|---|---|---|
| 3,834,048 | A | * | 9/1974 | Mauer | 36/50.1 |
| 3,927,665 | A | | 12/1975 | Wax | |
| 4,099,524 | A | | 7/1978 | Cueman et al. | |
| 4,475,543 | A | | 10/1984 | Brooks et al. | |
| 4,508,110 | A | * | 4/1985 | Modglin | 602/19 |
| 5,072,725 | A | | 12/1991 | Miller | |
| 5,074,288 | A | | 12/1991 | Miller | |
| 5,437,617 | A | * | 8/1995 | Heinz et al. | 602/19 |
| 5,634,891 | A | * | 6/1997 | Beczak et al. | 602/19 |
| RE35,940 | E | | 10/1998 | Heinz et al. | |
| 5,853,378 | A | | 12/1998 | Modglin | |
| 5,857,988 | A | * | 1/1999 | Shirley | 602/26 |
| 5,967,998 | A | * | 10/1999 | Modglin | 602/19 |
| 6,190,343 | B1 | * | 2/2001 | Heinz et al. | 602/19 |
| 6,213,968 | B1 | * | 4/2001 | Heinz et al. | 602/19 |
| 6,322,529 | B1 | * | 11/2001 | Chung | 602/19 |
| 6,478,759 | B1 | * | 11/2002 | Modglin et al. | 602/19 |
| 6,517,502 | B1 | * | 2/2003 | Heyman et al. | 602/5 |
| 6,676,620 | B1 | * | 1/2004 | Schwenn et al. | 602/12 |

(Continued)

*Primary Examiner*—Henry Bennett
*Assistant Examiner*—Amanda Wieker
(74) *Attorney, Agent, or Firm*—Dickstein Shapiro LLP

(57) ABSTRACT

A closure system for orthoses that permits a first body member conforming to a portion of a patient's torso to be connected through the closure system, with a second body member conforming to another portion of a patient's torso. The closure system includes a first connector member with a first series of plastic molded channels and a second connector member with a second series of plastic molded channels with an elongated flexible pull member operatively weaving around the respective first and second series of plastic molded channels to provide a mechanical force advantage when tightened by the patient to draw the first body member and the second body member against the patient's torso to exert compression forces. The elongated flexible pull member can comprise a cord such as a polyester cord with an exterior braided configuration.

12 Claims, 7 Drawing Sheets

U.S. PATENT DOCUMENTS

2002/0068890 A1* 6/2002 Schwenn et al. ............ 602/19

2002/0148461 A1* 10/2002 Heinz et al. ............... 128/96.1

* cited by examiner

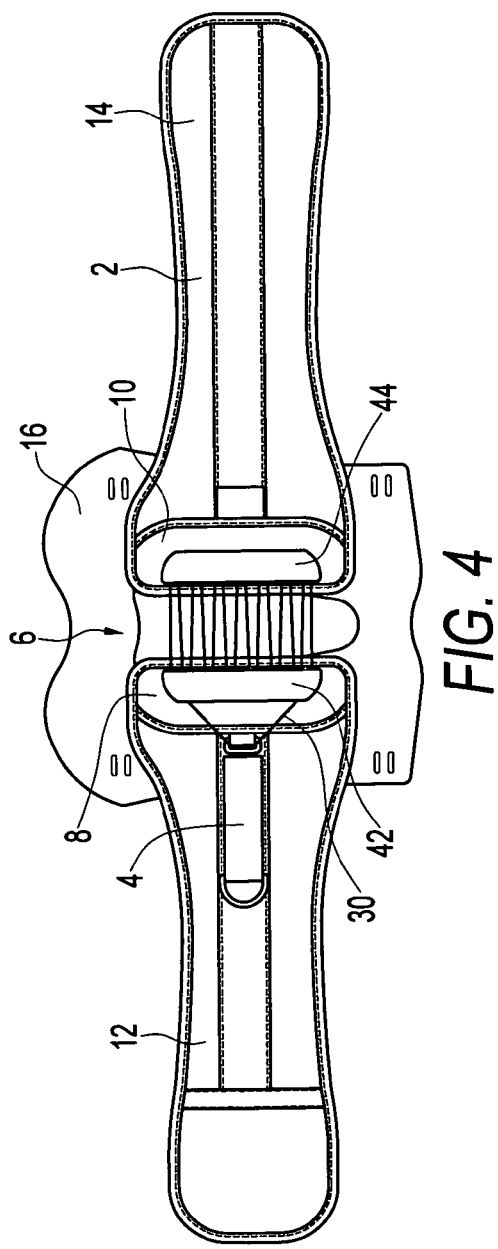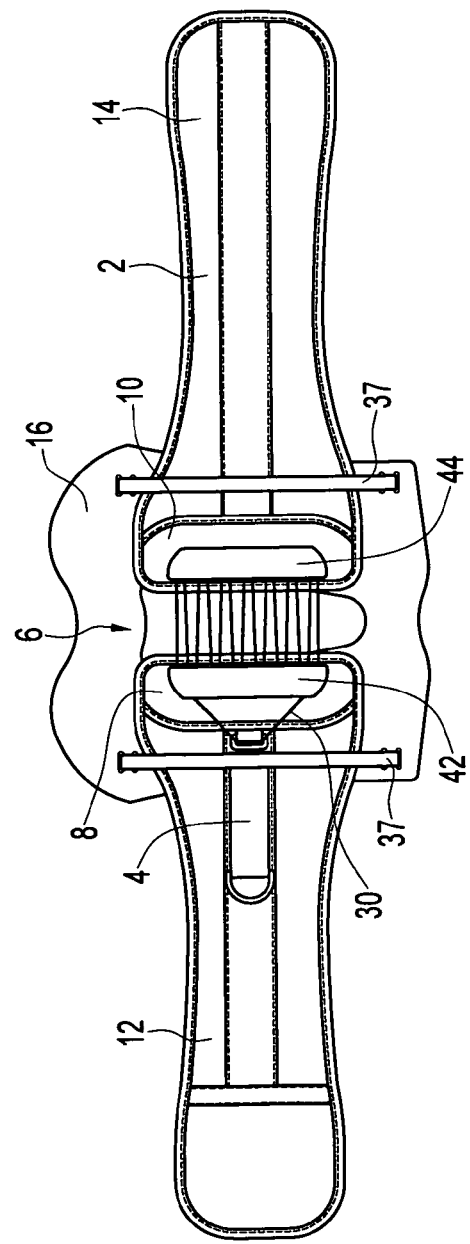

ORTHOSIS CLOSURE SYSTEM WITH MECHANICAL ADVANTAGE

This application claims the benefit of U.S. Provisional Application No. 60/501,026, filed Sep. 9, 2003, the entire disclosure of which is incorporated by reference herein.

BACKGROUND OF THE INVENTION

1. Field of the Invention

The present invention is directed to a closure system for orthoses with an improved pull system to provide a mechanical advantage for applying compression forces to a patient.

2. Description of the Related Art

Various types of orthotic systems have been suggested to address both injury and degenerate conditions that may occur—for example, a spinal orthosis to effectively stabilize the lumbo-sacral spine. Geriatric patients frequently experience chronic low back pain as a result of vertebral degeneration, discogenic disease and postural deterioration. Orthoses have been proposed to address stabilization of the lumbo-sacral spine and to assist in both pelvic tilt and rotational control. Such orthoses assist the patient in standing, sitting and prone positions by relieving postural stress pain. Various forms of back braces and corsets, both of a flexible and rigid configuration have been proposed, such as U.S. Pat. Nos. 5,072,725, 5,074,288, 4,508,110, 3,927,665, 4,099,524, 4,475,543, and 5,634,891. Frequently, patients with arthritic hands lack the dexterity to tighten and adjust such lumbo-sacral supports and other types of orthoses. Various forms of hook and pile or nap straps and closure systems, including hook and eye closure systems with buckles, are frequently utilized. Conventional corsets with lacing that is respectively looped through eyelets have provided a mechanical advantage when the lacing is tightened for patients. However, friction can be a factor between the lacing and the eyelets.

Other examples of lumbo-sacral orthoses can be found in U.S. Pat. Nos. 5,853,378, 5,967,998, 6,478,759, 5,437,617, 6,213,968 and U.S. Pat. No. Re. 35,940. In each of these patents, a mechanical advantage is secured by either pulling straps through a conventional buckle system on the '378, '998 and '759 patents, or by using a series of pulleys in the '617, '968 and '940 patents. Still further examples of orthoses with mechanical advantage closure systems can be found in U.S. Pat. No. 6,322,529, which uses swiveable eyelets or rings instead of pulleys, and U.S. patent application Publication No. 2002/0068890, which uses support posts instead of pulleys.

There is still a demand for relatively economical orthoses that can be conveniently used by a patient for a mechanical advantage in exerting compression and to provide a simplified and easily manufactured closure system.

SUMMARY OF THE INVENTION

The present invention provides a closure unit for orthoses such as a lumbo-sacral orthosis that permits a first body member conforming to a portion of a patient's torso to be connected through the closure unit, with a second body member conforming to another portion of a patient's torso. The closure system provides a mechanical advantage to assist the patient in tightening the orthosis.

The closure unit includes a first connector member with a first series of plastic molded channels and a second connector member with a second series of plastic molded channels with an elongated flexible pull member operatively weaving around the respective first and second series of plastic molded channels to provide a mechanical force advantage when tightened by the patient to draw the first body member and the second body member against the patient's torso to exert compression forces. The molded channels extend within a plastic member which can be contained with a plastic molded cap. The elongated flexible pull member can comprise a cord such as a polyester cord with an exterior braided configuration. The cord is connected at its distal end to a strap handle, which can receive a nap or hook material that can be appropriately positioned, for example, on the front body member, so that a patient who pulls the cord to tighten the osthosis can then secure it at a desired compression.

BRIEF DESCRIPTION OF THE DRAWINGS

Other features and advantages of the present invention will become apparent when the following detailed description is read in conjunction with the accompanying drawings, in which:

FIG. 3b shows an expanded front view of the back support member of FIG. 3a;

FIG. 4 is a front view of the orthosis of the present invention illustrated in connection with the back support member of FIG. 3a;

FIG. 5 is a front view of the orthosis of the present invention illustrated in connection with the back support member of FIG. 3a and with the straps of the back support member attached to the orthosis;

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide a modular spinal orthosis with an improved pull system to apply compression forces.

Figure 1:
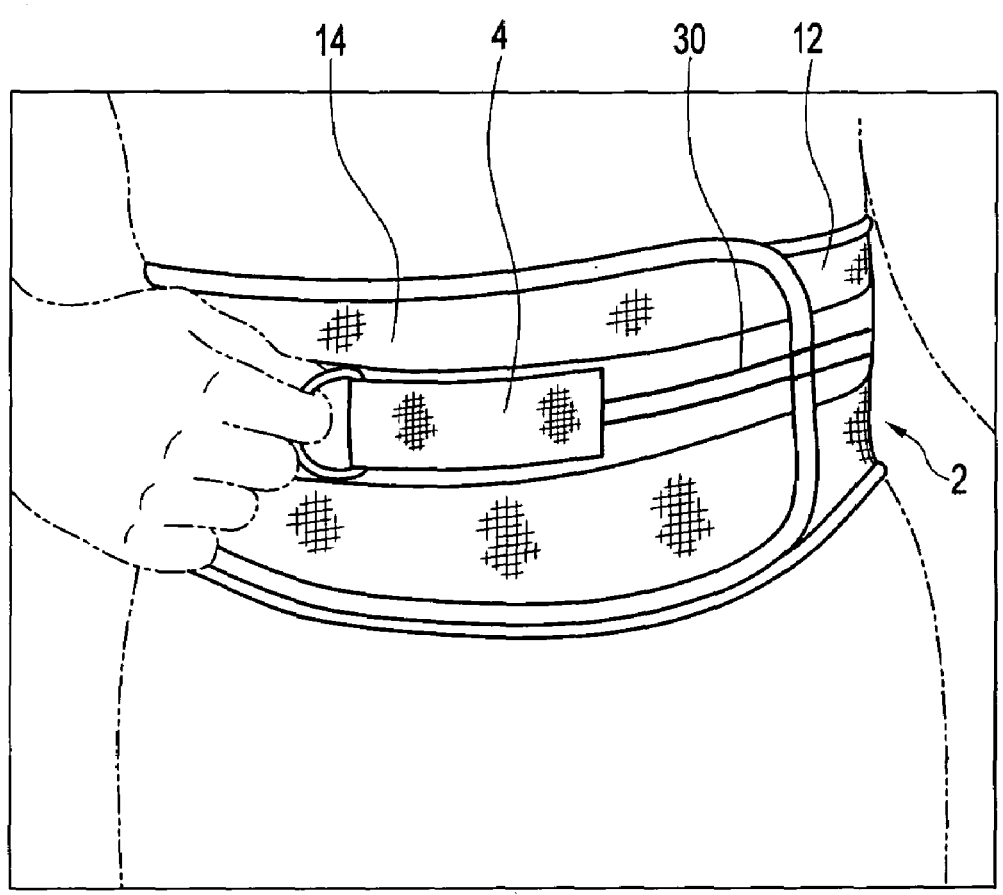
FIG. 1 is a front view of the orthosis of the present invention.
Figure 2:
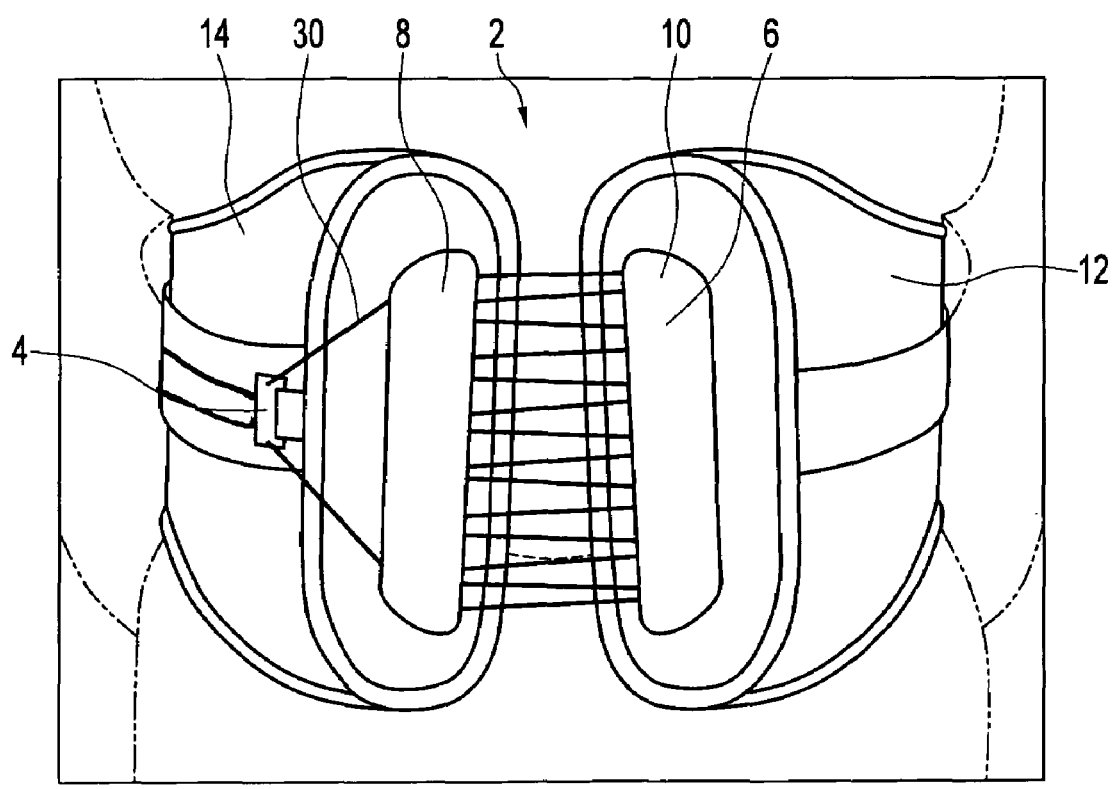
FIG. 2 is a rear view of the orthosis of the present invention.

A first embodiment of the present invention is disclosed in FIGS. 1 and 2 as a lumbo-sacral orthosis 2 which permits a patient to provide compressive forces about his/her torso by simply pulling and removably fastening a fastener member 4 to a surface portion of the orthosis. As can be seen in FIG. 2, a closure unit 6 includes a first connector member 8 and a second connector member 10. In the first embodiment, the orthosis can include a first body member 12 conforming to a portion of a patient's torso and a second body member 14 conforming also to another portion of a patient's torso, which is connected in the front using hook and pile. The orthosis has basically a belt-like configuration, and is provided with a separate rear body member 16 in the form of a malleable, but rigid chairback to provide back support, shown in FIGS. 3a and 3b. As can be appreciated, other arrangements can be provided, such that the rear body member, instead of having an exterior support member 16, lordotic pads can be placed in a series of elastic pockets and loops.

Figure 3B:
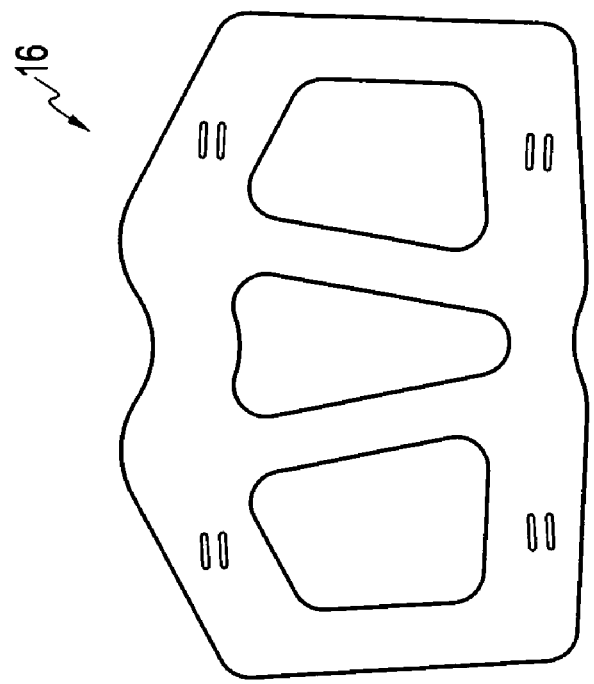
Figure 3A:
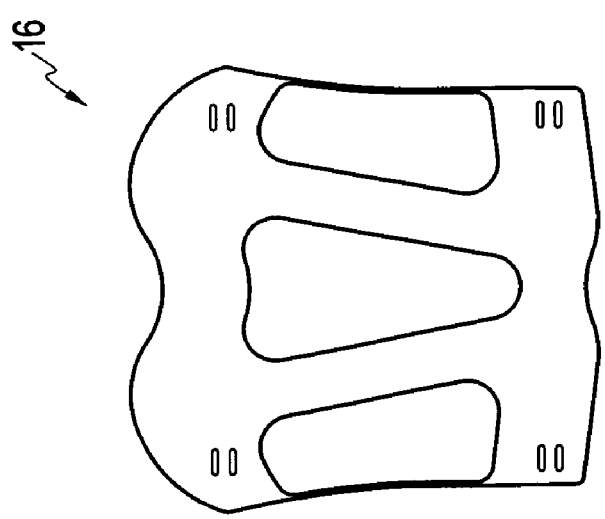
FIG. 3a shows a front view of the back support member used in the present invention.

FIGS. 4 and 5 illustrate the rear body member 16 of FIGS. 3a and 3b used in conjunction with the lumbo-sacral orthosis 2 of the present invention. FIGS. 4 and 5 illustrate front views of the orthosis 2 together with the back support member 16. As shown in FIG. 5, a plurality of attaching assemblies 37, for example VELCRO® straps 37, are attached to the back support member 16 to allow engagement of the orthosis 2 and to secure the first and second body members 12, 14 to the patient's torso. The straps 37 can be appropriately secured in position by securing the free ends of the straps to the orthosis 2.

Figure 6:
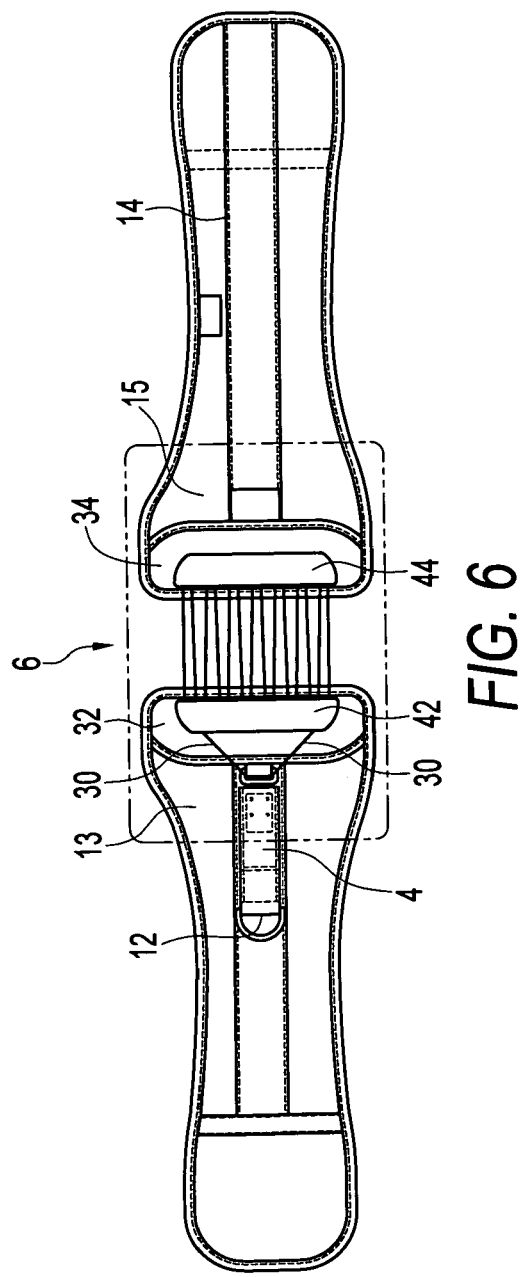
FIG. 6 is a front view of the orthosis of the present invention illustrating the closure unit with an elongated flexible member weaved around teardrop-shaped protuberances of the closure unit.
Figure 8:
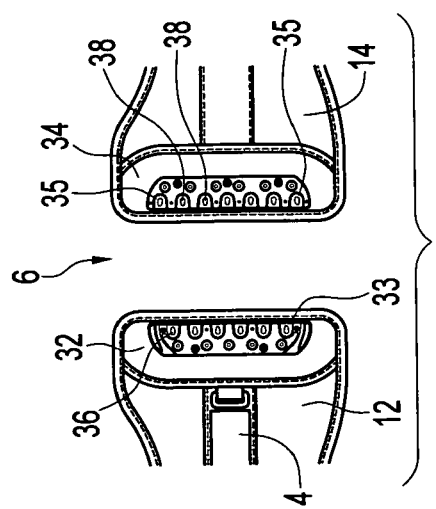
FIG. 8 is a partial front view of the closure unit of the orthosis of FIG. 6 without the top molded caps.
Figure 7:
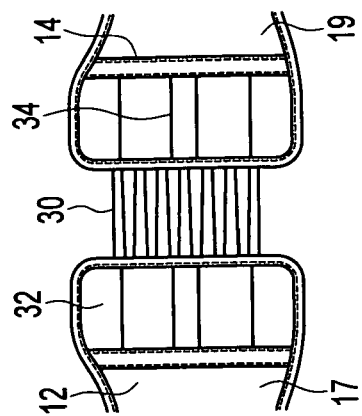
FIG. 7 is a partial back view of the closure unit of the orthosis of FIG. 6.

Referring to FIGS. 6–8, and in accordance with an embodiment of the present invention, the closure unit 6 includes first and second plastic connector members 32, 34 provided on a top surface 13, 15 of the first and second members 12, 14. In a preferred embodiment, the first and second plastic connector members 32, 34 are provided with first and second plastic molded caps or members 42, 44, which cover areas where first and second series of C-shaped channels 33, 35 are formed according to embodiments of the present invention. FIG. 6 illustrates first and second plastic molded caps 42, 44 covering the areas of the first and second plastic connector members 32, 34 where first and second series of C-shaped channels 33, 35 are formed. FIG. 7 illustrates a partial back view of the closure unit 6 of FIG. 6 with the first and second plastic connector members 32, 34 provided on a bottom surface 17, 19 of the first and second members 12, 14. FIG. 8 illustrates a top view of the closure unit 6 of FIG. 6 but with the first and second plastic molded caps 42, 44 removed.

Figure 9B:
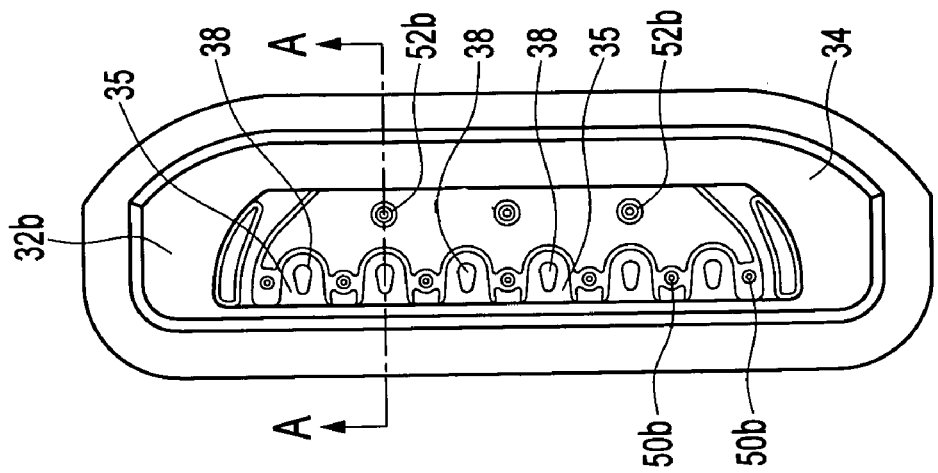
FIG. 9b is a partial enlarged view of the right connector member of the closure unit of the orthosis of FIG. 8, showing the channels created by the teardrop plastic molding.
Figure 9A:
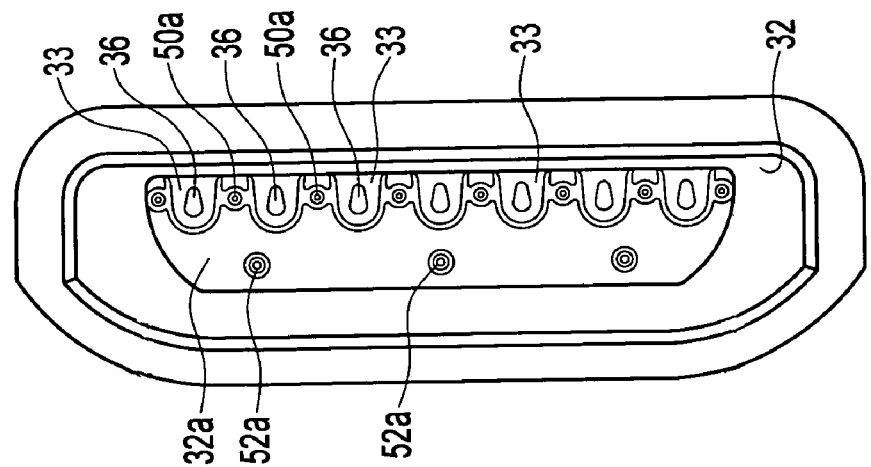
FIG. 9a is a partial enlarged view of the left connector member of the closure unit of the orthosis of FIG. 8, showing the channels created by the teardrop plastic molding.

As shown in FIG. 8, the first and second plastic connector members 32, 34 include respective first and second series of channels 33, 35 formed by first and second plurality of C-shaped walls 63, 65 spaced from a corresponding first and second series of plastic molded protuberances 36, 38 having a teardrop shape. As illustrated in FIGS. 8 and 9a, 9b, the C-shaped walls 63, 65 extend to edge 65a, 65b of each of plastic members 32a, 32b. Plastic molded teardrops 36, 38 may be clear and may extend perpendicular to the top surface 13, 15 of respective first and second members 12, 14. Although FIG. 8 illustrates a series of six plastic molded teardrops 36 on the first connector member 32 and a series of seven plastic molded teardrops 38 on the second connector member 34, it must be understood that the invention contemplates a closure unit having any number of plastic molded teardrops on each of the connector members. In addition, the plastic molded teardrops of the closure unit of the present invention may be employed in conjunction with other plastic molded protuberances which may have various shapes and geometries.

Also illustrated in FIGS. 6 and 7 is an elongated flexible member or cord 30, which can be formed from a polyester material having an exterior braided surface to thereby provide a low friction, but strong, pull member such as a Harness cord with a diameter of 0.039–0.044 inches and a 98 lb. test strength. The cord member 30 slides within the respective channels 33, 35 in each of the connector members to thereby reduce the friction of a normal corset, while also providing a mechanical advantage or force multiplier when the cord 30 is pulled by the patient.

The cord 30 is connected at its end to a strap handle 4 in the form of an eyelet. The user, by pulling upon the strap, can then employ a mechanical advantage, via cord 30 and the channels 33, 35 formed by plastic molded teardrops 36, 38, to pull the respective first body member 12 and second body member 14 together to provide a compressive force. The strap can then be appropriately secured in position by securing the free end of the strap to the orthosis using hook and pile.

The ability of the cord 30 to slide with low friction within the plastic molded channels 33, 35 provides a relatively compact efficient mechanical advantage without requiring additional moving parts such as pulleys or posts. Thus, a relatively economical and compact adjustable lumbo-sacral orthosis with an improved closure unit is provided.

FIGS. 9a and 9b illustrate in more detail the plastic molded channels and teardrops of the present invention extending through each of the first and second connecting members of the present invention. FIG. 9a illustrates the first connecting member 32 formed of plastic member 32a mechanically attached to the orthosis 2 by fastening elements 50a, for example screws, and rivets 52a. Plastic molded channels 33 and teardrops 36 are provided within plastic member 32a. Subsequently, plastic molded cap or member 42 (FIGS. 4–6) is juxtaposed over the plastic member 32a and secured by fastening elements 50a and rivets 52a. Again, although FIG. 9a illustrates seven teardrops 36 and corresponding plastic molded channels 33, the invention contemplates any number of such channels and teardrop protuberances.

FIG. 9b illustrates the second connecting member 34 formed of plastic member 32b mechanically attached to the orthosis 2 by fastening elements 50b, for example screws, and rivets 52b. Plastic molded channels 35 and teardrops 38 are provided within plastic member 32b. Subsequently, plastic molded cap or member 44 (FIGS. 4–6) is juxtaposed over the plastic member 32b and secured by fastening elements 50b and rivets 52b. Again, although FIG. 9b illustrates six teardrops 38 and corresponding plastic molded channels 35, the invention contemplates any number of such channels and teardrop protuberances.

Figure 10:
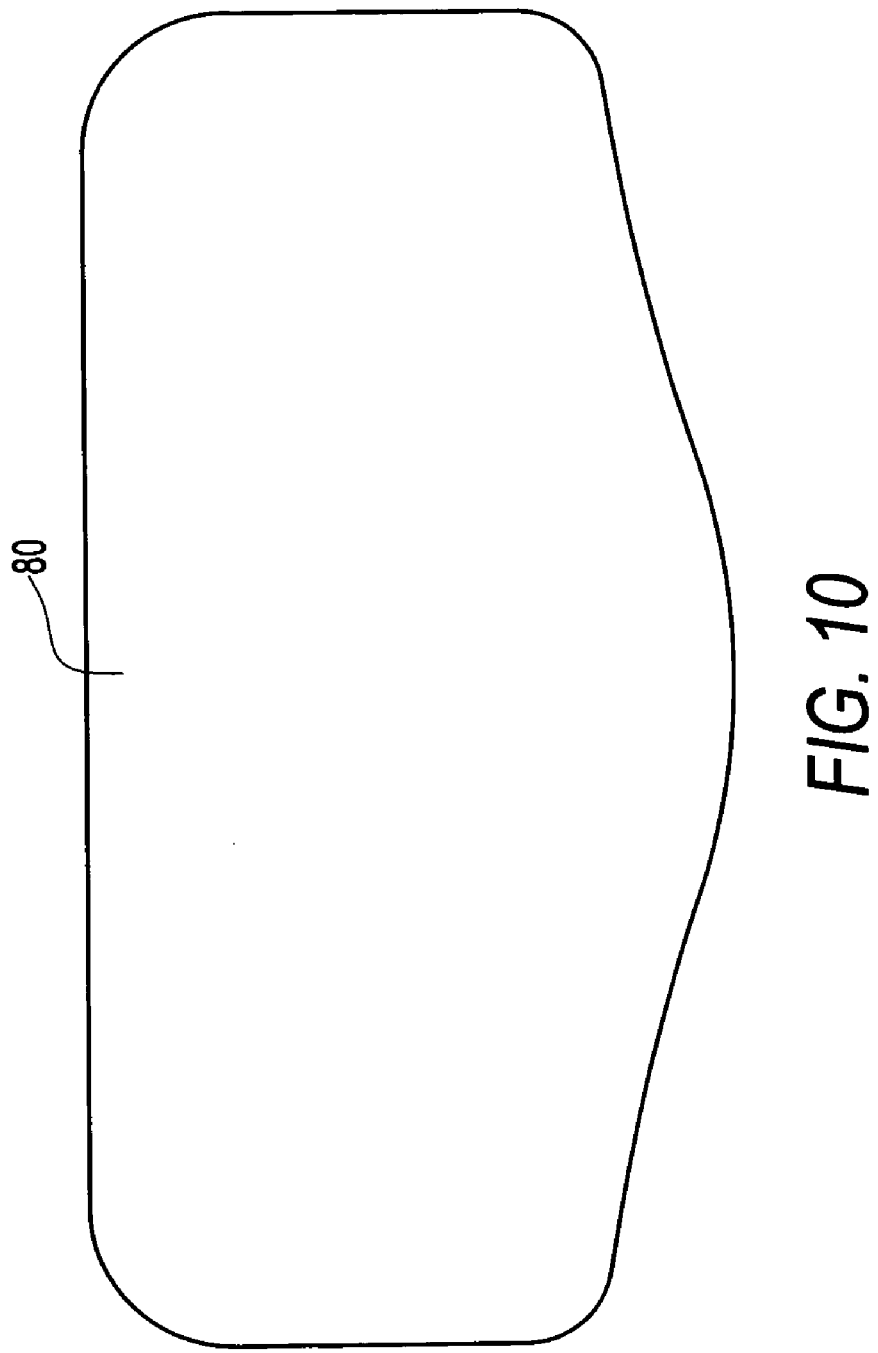
FIG. 10 is a front view of the anterior panel used in connection with the orthosis of the present invention.

FIG. 10 illustrates a front view of an anterior panel 80 which may be used in connection with the orthosis 2 of the present invention. The anterior panel 80 may be formed of a material similar to, or different from, the material of the rear body member 16. Preferably, the anterior panel 80 may be formed of a malleable, but rigid material and may be provided in the front of the patient's torso, more specifically, between the orthosis 2 of the present invention and the patient's torso.

Although the invention has been described above with reference to a closure system for a specific orthosis, such as the closure unit 6 for the lumbo-sacral orthosis 2 of FIGS. 1–9, it must be understood that the invention is not limited to the above-described embodiment. Accordingly, the invention also contemplates embodiments wherein the closure system of the invention applies to various types of orthoses for other parts of a patient's body in addition to the spine, such as a leg brace or a shoulder brace, among others. In addition, the closure system of the present invention may be applied to orthoses used in conjunction with therapeutic heating and cooling devices. For example, a cooling mechanism which utilizes a circulating coolant can be applied posteriorly of the lumbo-sacral orthosis 2 to reduce swelling, facilitate pain relief or to serve other purposes by causing cooling of the individual's back. Similarly, a heating pad or gel may be used for therapeutic purposes.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. An orthosis apparatus, comprising:
    a first segment conforming to a first region of a patient's body;
    a second segment conforming to a second region of the patient's body; and
    a closure system comprising:
        a first connector member having a first plurality of plastic molded covered C-shaped channels, each of the plastic molded covered C-shaped channels being formed by C-shaped walls spaced from a plurality of corresponding plastic molded teardrop-shaped protuberances, the plastic molded covered C-shaped channels being operatively connected to the first segment and respectively extending around the corresponding plurality of teardrop-shaped protuberances;
        a second connector member having a second plurality of plastic molded covered C-shaped channels, each of the plastic molded covered C-shaped channels being formed by C-shaped walls spaced from a plurality of corresponding plastic molded teardrop-shaped protuberances, the plastic molded covered C-shaped channels being operatively connected to the second segment and respectively extending around the corresponding plurality of teardrop-shaped protuberances; and
        an elongated flexible pull member operatively extending through, and guided by, the first and second plurality of plastic molded covered C-shaped channels to provide a mechanical force when tightened by the patient to adjust the position of the first segment relative to that of the second segment, wherein the C-shaped walls forming the first plurality of plastic molded covered C-shaped channels extend to an edge of the first connector member wherein the elongated flexible pull member is received, and wherein the C-shaped walls forming the second plurality of plastic molded covered C-shaped channels extend to an edge of the second connector member wherein the elongated flexible pull member is received, so that the C-shaped walls and the plurality of corresponding plastic molded teardrop-shaped protuberances restrict movement of the flexible pull member within the first and second plurality of plastic molded covered C-shaped channels.

2. The orthosis apparatus of claim 1, wherein the closure system further comprises a flexible strap operatively connected to the elongated flexible pull member to provide tension to the elongated flexible pull member.

3. The orthosis apparatus of claim 1, wherein at least one of the teardrop-shaped protuberances is formed of a dear plastic material.

4. A lumbo-sacral orthopedic brace, comprising:
    a first segment conforming to a first region of a patient's torso, the first segment including a first plurality of plastic molded covered C-shaped channels formed by C-shaped walls spaced from a plurality of corresponding plastic molded teardrop-shaped protuberances, the plastic molded covered C-shaped channels respectively extending around the corresponding plurality of teardrop-shaped protuberances extending perpendicular to a surface of the first segment;
    a second segment conforming to a second portion of the patient's torso, the second segment including a second plurality of plastic molded covered C-shaped channels formed by C-shaped walls spaced from a plurality of corresponding plastic molded teardrop-shaped protuberances, the plastic molded covered C-shaped channels respectively extending around the corresponding plurality of teardrop-shaped protuberances extending perpendicular to a surface of the second segment; and
    an elongated flexible pull member operatively extending through, and guided by, the plastic molded covered C-shaped channels and around the first and second plurality of teardrop-shaped protuberances, to allow the first and second segments to be detachably connected together around the patient's torso, wherein the C-shaped walls forming the first plurality of plastic molded covered C-shaped channels extend to an edge of the first connector member wherein the elongated flexible pull member is received, and wherein the C-shaped walls forming the second plurality of plastic molded covered C-shaped channels extend to an edge of the second connector member wherein the elongated flexible pull member is received, so that the C-shaped walls and the plurality of corresponding plastic molded teardrop-shaped protuberances restrict movement of the flexible pull member within the first and second plurality of plastic molded covered C-shaped channels.

5. A lumbo-sacral orthopedic brace, comprising:
    a first segment conforming to a first region of a patient's torso, the first segment including at least a first plastic molded covered C-shaped channel being formed by a C-shaped wall spaced from a corresponding plastic molded protuberance having a teardrop configuration, the first plastic molded covered C-shaped channel being defined by and extending around at least the first plastic molded protuberance having a teardrop configuration;
    a second segment conforming to a second portion of the patient's torso, the second segment including at least a second plastic molded covered C-shaped channel being formed by a C-shaped wall spaced from a corresponding plastic molded protuberance having a teardrop configuration, the second plastic molded covered C-shaped channel being defined by and extending around at least the second plastic molded protuberance having a teardrop configuration; and
    means for allowing the first and second segments to be detachably connected together around the patient's torso, including a cord operatively connected to the first and second segments, the cord passing through, and guided by, the at least first and second covered plastic molded C-shaped channels and wrapping around the at least first and second protuberances having teardrop configurations, wherein the C-shaped walls forming the at least first plastic molded covered C-shaped channel extend to an edge of the first connector member wherein the cord is received, and wherein the C-shaped walls forming the at least second plastic molded covered C-shaped channel extend to an edge of the second connector member wherein the cord is received, so that the C-shaped walls and the plurality of corresponding plastic molded teardrop-shaped protuberances restrict movement of the cord within the plastic molded covered C-shaped channels.

6. The lumbo-sacral orthopedic brace of claim 5, wherein the means for allowing the first and second segments to be detachably connected together further comprises:

a strap connected to the cord for applying tension to the cord to bring the first and second segments closer together on the patient's torso.

7. The lumbo-sacral orthopedic brace of claim 6, wherein the cord is formed of polyester material.

8. The lumbo-sacral orthopedic brace of claim 7, wherein the cord has a braided surface.

9. The lumbo-sacral orthopedic brace of claim 5, wherein the first and second segments are formed of a plastic material.

10. A method for assembling a closure system for art orthosis, comprising the steps of:

providing a first connector member having a first plurality of plastic molded protuberances having a teardrop shape, the first plurality of protuberances defining a first plurality of plastic molded C-shaped channels, the first plurality of C-shaped channels being further defined by a first plurality of C-shaped walls spaced from the first plurality of plastic molded protuberances;

providing a second connector member having a second plurality of plastic molded protuberances having a teardrop shape, the second plurality of protuberances defining a second plurality of plastic molded C-shaped channels, the second plurality of C-shaped channels being further defined by a second plurality of C-shaped walls spaced from the first plurality of plastic molded protuberances; and wrapping a pull member around the first and second plurality of protuberances having a teardrop shape to allow the pull member to slide within, and be guided by, the first and second plurality of plastic molded C-shaped channels, wherein each of the first and second plurality of C-shaped walls extends to an edge of the first connector member wherein the pull member is received, and wherein each of the second plurality of C-shaped walls extends to an edge of the second connector member wherein the pull member is received, so that the C-shaped walls and the corresponding plastic molded protuberances having a teardrop shape restrict movement of the pull member within the first and second plurality of plastic molded C-shaped channels.

11. The method of claim 10, wherein the pull member is formed of polyester material.

12. The method of claim 10, wherein the pull member has an outer surface that is braided.

* * * * *